United States Patent [19]

Grasdepot

[11] Patent Number: 5,506,685
[45] Date of Patent: Apr. 9, 1996

[54] METHOD AND APPARATUS FOR DETERMINING THE ABSORPTION OF ELECTROMAGNETIC RADIATION BY A GAS

[75] Inventor: François Grasdepot, Fontenay-aux-Roses, France

[73] Assignee: Schlumberger Industries, S.A., Montrouge, France

[21] Appl. No.: 396,840

[22] Filed: Mar. 1, 1996

[30] Foreign Application Priority Data

Mar. 3, 1994 [FR] France ................... 94 02578

[51] Int. Cl.$^6$ ................... G01N 21/31; G01N 21/35
[52] U.S. Cl. ................ 356/409; 250/339.13; 250/565; 356/435; 356/437
[58] Field of Search ................... 356/409, 436, 356/437, 435; 250/339.06, 339.13, 345, 565

[56] References Cited

U.S. PATENT DOCUMENTS

5,387,979   2/1995   Brauer et al. ................ 356/437 X

*Primary Examiner*—Vincent P. McGraw
*Attorney, Agent, or Firm*—Keith G. W. Smith

[57] ABSTRACT

The invention provides a method consisting successively in producing two electromagnetic radiations of the same wavelength that is modulated as a function of time over a range of wavelengths, a "measurement" one of said radiations passing through a gas that presents selective absorption for said radiation in the range, while the other radiation constitutes a "reference" radiation. Each of said radiations is transformed into a respective "measurement" or "reference" electrical signal. The measurement signal is divided by the reference signal to obtain a first quotient electrical signal which is in turn split into two portions: a time-varying AC portion and a DC portion that does not vary with time. The AC portion is divided by said DC portion in order to obtain a second quotient electrical signal representative solely of the electromagnetic radiation absorbed by the gas.

14 Claims, 6 Drawing Sheets

METHOD AND APPARATUS FOR DETERMINING THE ABSORPTION OF ELECTROMAGNETIC RADIATION BY A GAS

The present invention relates to a method of determining the absorption of electromagnetic radiation of wavelength that is variable over a range of wavelengths by a gas that presents selective absorption of the radiation over said range of wavelengths. The invention also relates to apparatus for implementing the method.

BACKGROUND OF THE INVENTION

It is known that certain gases absorb electromagnetic radiation in selective manner as a function of the wavelength of said radiation when the substances concerned have a spectrum structure comprising lines that are relatively fine and separate, in contrast to a structure comprising bands.

This property is used to determine the absorption due to such substances, and thus to deduce the concentration thereof.

There is frequently a need to determine the concentration of a gas in a mixture with other gases without performing analyses that would require physical contact with the fluid. In any event, such analysis is not always easy when, for example, it is desired to detect a gas leak quickly.

Various physical methods are known for determining the concentration of a gas that possesses selective absorption for electromagnetic radiation over a range of wavelengths of the radiation.

Such physical methods enable measurement to be performed without making contact with the gas, unlike chemical measurements, and in addition they present good selectivity.

For example, a reliable method is known that is based on a Fourier transform interferometer and that consists in determining all of the absorption characteristics of the gas over a wide range of optical wavelengths. Nevertheless, that method is very complex.

It is also known chat the emission wavelength of a laser diode can be modulated (by modulating the injection current and/or the temperature of the laser) over a range of wavelengths that includes an absorption line of a gas whose concentration is to be determined, and to cause the modulated optical radiation emitted by the laser diode to pass through a cell that is filled with gas. An optical detector then serves to pick up optical radiation of varying amplitude that is characteristic of the gas and of its concentration.

Unfortunately, in general, the detected radiation is constituted by radiation due to modulation of the laser plus peaks superposed thereon due to differential absorption of the gas (with both kinds of radiation being attenuated by constant losses that are a function of wavelength and that are due to the various forms of opaqueness encountered by the modulated optical radiation coming from the laser diode), and it is therefore not possible to isolate the contribution in said radiation that is due solely to the gas.

A known method is mentioned in the article "Absorption measurements of water-vapor concentration, temperature, and line-shape parameters using a tunable InGaAsP diode laser", Applied Optics, Vol. 32, No. 30, pp. 6104–6116, Oct. 20, 1993, and which uses optical means to determine the concentration of water vapor while avoiding some of the problems mentioned above.

In that method, a laser diode is used and its emission wavelength is modulated by modulating the injection current and/or the temperature of the laser, with a range of wavelengths being chosen that covers the range of wavelengths over which water vapor presents differential absorption.

That laser diode emits modulated optical radiation which is subsequently split into two modulated optical radiations, one acting as reference radiation while the other passes through a cell filled with a gaseous mixture containing the water vapor whose concentration is to be determined, and thus acts as a measurement radiation.

At the output from the gas cell, an optical radiation detector picks up the measurement optical radiation of varying amplitude that is characteristic of water vapor and of its concentration, and transforms it into a measurement electrical signal. The reference radiation is also picked up by another optical radiation detector and it is transformed into a reference electrical signal.

The method described then consists in subtracting the measurement signal from the reference signal and in dividing the resulting electrical signal by the reference signal to deduce therefrom what optical radiation has been absorbed by the water vapor, and thus deduce the concentration thereof.

Nevertheless, that article specifies that in order to obtain a reliable absorption measurement, it is necessary for the amplitude of the two electrical signals from the two optical radiation detectors to be accurately balanced.

The slightest difference in amplification gain between them gives rise to distortion of the absorption measurement.

In addition, in the time interval between balancing the signals and obtaining the absorption measurement, any change in optical losses is confused with variation of said absorption to the detriment of measurement accuracy.

It is also specified in that article that various techniques have been tried for accurately balancing the electrical signals from the optical radiation detectors, but that none has given entire satisfaction. That problem is general to prior art absorption measurement methods and it can be asserted that methods known in the state of the art do not make it possible to determine absorption simply and reliably, and therefore do not make it possible to determine the concentration of a gas that presents selective absorption in a given range of wavelengths of electromagnetic radiation, since such methods cannot avoid being sensitive to inevitable parasitic losses.

OBJECTS AND SUMMARY OF THE INVENTION

The present invention therefore seeks to remedy the above drawbacks by proposing both a method of determining the absorption of electromagnetic radiation of wavelength that is variable over a range of wavelengths by a gas that presents selective absorption of said radiation over said range of wavelengths, and apparatus for implementing said method, both of which are simple and independent of parasitic attenuations and losses to which the electromagnetic radiation and the electrical signals are subject.

The present invention thus provides a method of determining the absorption of electromagnetic radiation of wavelength that is variable over a range of wavelengths by a gas that presents selective absorption of said radiation in said range of wavelengths, the method consisting successively in:

producing two electromagnetic radiations of the same wavelength that is modulated as a function of time over the range of wavelengths, one of said electromagnetic radiations passing through said gas and being referred to as a "measurement" radiation, while the other electromagnetic radiation is referred to as a "reference" radiation;

detecting each of the measurement and reference electromagnetic radiations and transforming them into respective electrical signals referred to as a "measurement" signal Mes(t) and as a "reference" signal Ref(t);

dividing said measurement electrical signal Mes(t) by said reference electrical signal Ref(t), thereby obtaining a first quotient electrical signal Div1(t) made up of a time-varying AC portion and a non-time-varying DC portion;

separating said AC and DC portions; and dividing the AC portion of the first quotient electrical signal Div1(t) by the DC portion of the same signal in order to obtain a second quotient electrical signal Div2(t) representative solely of the absorption of electromagnetic radiation by said gas.

The method of the invention is thus very simple to implement and is insensitive to parasitic attenuations and losses to which the electromagnetic radiation and the electrical signals are subject. The electrical signal obtained in this way is representative of a magnitude that relates directly to the concentration of the gas and that can easily be used for accurately determining said concentration of the gas.

Better results are thus obtained than in the prior art while using techniques that are simpler than those that have been proposed in the past.

According to other features of the invention:

the two electromagnetic radiations have amplitudes whose quotient is constant over time;

the two electromagnetic radiations are produced from a source that emits base electromagnetic radiation, which base electromagnetic radiation is split in order to obtain said measurement and reference electromagnetic radiations;

the electromagnetic radiation is optical radiation;

the optical source is a laser diode which is injection current and/or temperature modulated; and the AC and DC portions are separated by electrical filtering.

The present invention also provides apparatus for determining the absorption of electromagnetic radiation of wavelength variable over a range of wavelengths by a gas that presents selective absorption of said radiation in said range of wavelengths, for the purpose of implementing the method described above, and comprising:

means for producing two electromagnetic radiations of the same wavelength that is modulated as a function of time over the range of wavelengths, one of said electromagnetic radiations passing through said gas and being referred to as the "measurement" radiation, the other electromagnetic radiation being referred to as the "reference" radiation;

means for detecting each of the measurement and reference electromagnetic radiations and for transforming said radiations into respective electrical signals referred to as the "measurement" signal and as the "reference" signal;

first divider for dividing the measurement electrical signal by the reference electrical signal so as to obtain a first quotient electrical signal constituted by a time-varying AC portion and a non-time-varying DC portion;

separator means for separating the AC and DC portions of the first quotient electrical signal; and second divider for dividing the AC portion of said first quotient electrical signal by the DC portion of the same signal in order to obtain a second quotient electrical signal representative solely of the absorption of the electromagnetic radiation by the gas.

This apparatus presents the advantage of being particularly simple in design and does not require electronic means that are complex, bulky, or expensive.

According to the invention, the means for producing two electromagnetic radiations comprise a source emitting base electromagnetic radiation together with splitting means for splitting said base radiation to obtain said measurement and reference electromagnetic radiations. The electromagnetic radiation is optical radiation.

The splitting means are constituted by a glass plate placed on the path of the base optical radiation at an inclination to said radiation and possessing on that one of its faces which receives said signal a semitransparent metal deposit in order to increase reflection from said face.

The optical source is a laser diode provided with a system for modulating the optical wavelength of the base optical radiation by injection current and/or temperature modulation.

The means for detecting the measurement and reference optical radiations and for transforming said radiations into electrical signals are constituted by photodiodes of the same type.

According to other features of the invention:

the means for separating the AC and DC portions of the first quotient electrical signal comprise a first electrical filter for selecting the AC portion of said signal and a second electrical filter for selecting the DC portion of the signal;

the first electrical filter is constituted by a capacitor and a resistor constituting a highpass filter; and the second electrical filter is constituted by a resistor and a capacitor forming a lowpass filter.

A particularly advantageous application of the invention lies in determining the concentration of a specific gas such as methane or carbon monoxide in a mixture with other gases, e.g. for billing purposes, or when it is desired to detect a leak of the gas.

Once the absorption of optical radiation by a gas has been determined in application of the invention, it is then easy to deduce therefrom a metrologically reliable value for the concentration of the gas, and this is independent of whether the concentration of said gas is low or high.

BRIEF DESCRIPTION OF THE DRAWINGS

Other characteristics and advantages appear from the following description given by way of non-limiting example and made with reference to the accompanying drawings, in which.

MORE DETAILED DESCRIPTION

Figure 1:
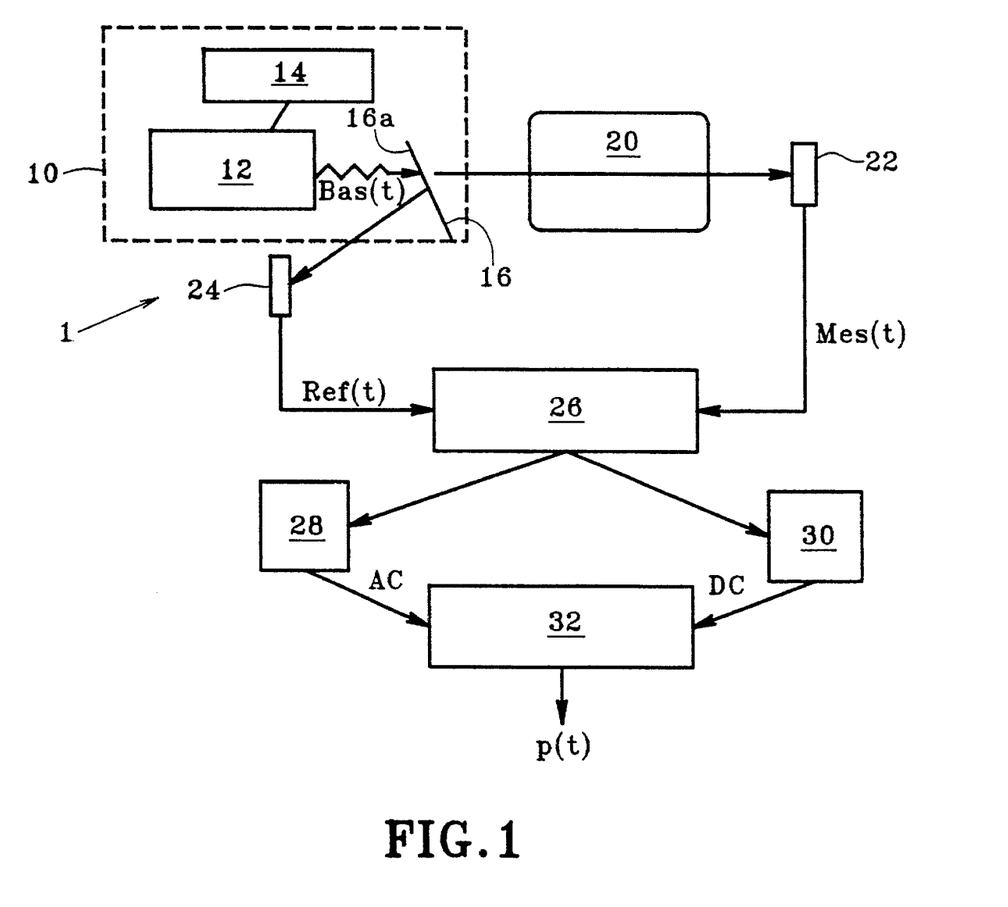
FIG. 1 is a block diagram of various elements constituting the apparatus of the invention.

As shown in FIG. 1 and given overall or general reference 1, the apparatus of the invention applies to methane which presents selective absorption of optical radiation of wavelength varying over a range of optical wavelengths. The range of optical wavelengths is selected in such a manner as to contain at least one wavelength 10 for which methane possesses an absorption line. By way of example, this wavelength $\lambda_0$ is equal to 1.333 μm, and the range of wavelengths covers, for example, the following range: $\lambda_0 - \Delta\lambda = 1.332$ μm to $\lambda_0 + \Delta\lambda = 1.334$ μm The apparatus includes means 10 for producing two optical radiations: one is referred to as the "measurement" optical radiation and is written Mes(t), and the other is referred to as the "reference" optical radiation and is written Ref(t). These two optical radiations come from a base optical radiation Bas(t) emitted by an optical source which, for example, may be a conventional monomode laser diode 12. The laser diode 12 may be fitted, for example, with a power supply and modulator system 14 sold by Laser 2000 under the reference OEM Dylor LT20-200 and serving to power said diode and to modulate the emission wavelength of said diode in time-varying manner over the above-mentioned range of optical wavelengths. The modulation system 14 keeps the laser diode at a constant temperature while the electrical current flowing through the junction of the diode is modulated about a predefined value i0, e.g. equal to 50 mA, with the modulation having an amplitude Di that is a function of time and periodic, with a period T=0.1 ms: $i(t)=i0+\Delta i(t)$. The value of the maximum amplitude of $\Delta i(t)$ is equal to 30 mA, for example, the appearance of the signal representing the electrical current may be that of a sawtooth, for example. The wavelength 1 of the base optical radiation Bas(t) emitted by the laser diode and the energy E of said radiation are likewise functions of time, that are periodic, and that have the same period T.

Figure 2:
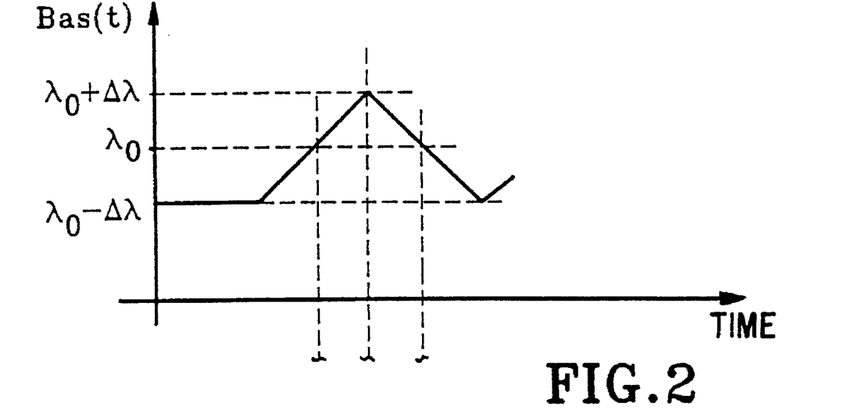
FIG. 2 shows the electrical signal corresponding to the modulated emission optical radiation.

FIG. 2 shows the appearance of the electrical signal corresponding to the modulated base optical radiation Bas(t).

The modulated base optical radiation Bas(t) is then optically split by optical splitting means constituted, for example, by a semitransparent glass plate 16 referred to as a splitting plate disposed on the path of said base optical radiation, as shown in FIG. 1. The glass plate is at an angle to the base optical radiation and its face 16a exposed to said base optical radiation is covered in a metal deposit that serves to increase the reflecting power of said face.

By way of example, the glass plate is 1 mm thick and it is covered in a thin film of gold having thickness equal to 60 nm.

A portion of the base optical radiation passes through the glass plate 16 and gives rise to the measurement optical radiation Mes(t). To clarify the explanation, the measurement optical radiation and the measurement electrical signal are both designated by the same term "Mes(t)", and the same applies to the reference optical radiation and the reference electrical signal which are both referred to as "Ref(t)".

The apparatus of the invention also includes a cell 22 containing a mixture of gas, and in particular containing methane. This cell is placed on the path of the measurement optical radiation Mes(t) in such a manner that said radiation is affected by the presence of methane.

Figure 3:
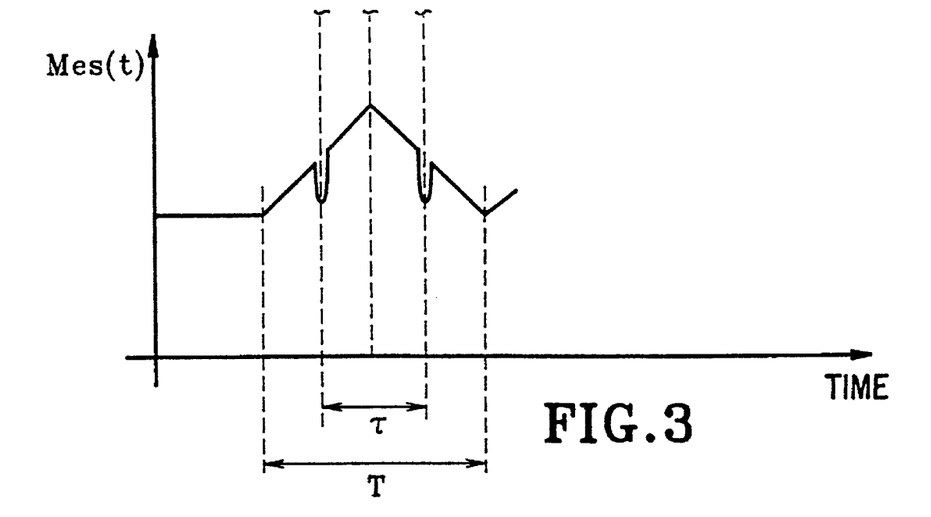
FIG. 3 shows the electrical signal corresponding to the measurement optical radiation after it has passed through the gas cell.

Optical detection means formed by an InGaAs photodetector 22 pick up the measurement optical radiation after it has passed through the cell 20, and transform it into a measurement analog electrical signal having the appearance shown in FIG. 3. When compared with the appearance of the signal in FIG. 2, it can be seen that inverted peaks are superposed on the base signal, which peaks correspond to the absorption line of methane. The measurement electrical signal is given by the following equation:

$$Mes(t) = T \cdot G[\lambda(t)] \cdot E(t)$$

where T represents the total optical and electrical attenuation to which the measurement optical radiation and the measurement signal are subjected from the optical emission, and G represents the optical transmission due to the gas on passing through the cell 20. The optical transmission is expressed as a function of the optical absorption:

$$p[\lambda(t)]$$

Consequently, the measurement electrical signal is written:

$$Mes(t) = T \cdot (1 - p[\lambda(t)]) \cdot E(t)$$

After optical splitting, a reference optical radiation Ref(t) is also obtained which is reflected from the coated face 16a of the glass plate, and this radiation is subsequently optically detected by optical detection means formed, for example, by a conventional InGaAs photodiode 24 identical to the photodiode 22 and placed on the path of the reflected optical radiation.

Figure 4:
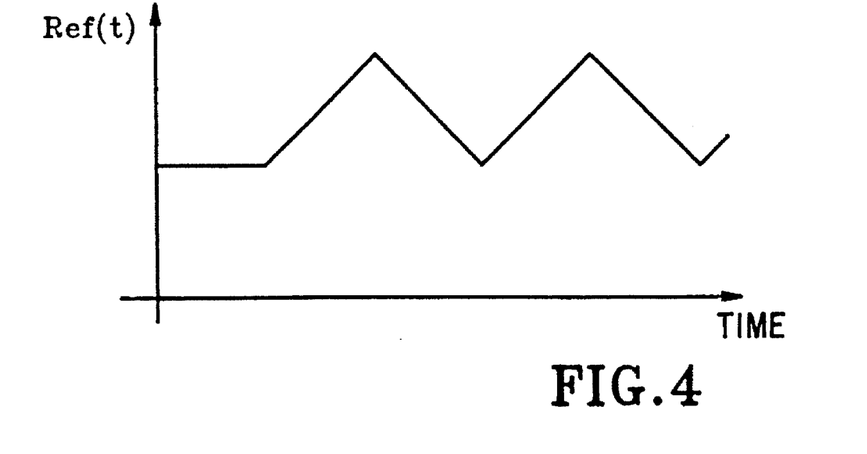
FIG. 4 shows the electrical signal corresponding to the reference optical radiation.

The reference optical radiation is transformed into a reference analog electrical signal Ref(t) at the output from the photodiode 24, which reference electrical signal can be expressed as follows:

$$Ref(t) = R \cdot m(t)$$

where R designates the total optical and electrical attenuation to which the reference radiation and the reference signal have been subjected since the optical emission. The appearance of this signal is shown in FIG. 4.

As shown in FIG. 1, the apparatus of the invention includes a first divider for dividing the measurement electrical signal by the reference electrical signal to obtain a first quotient electrical signal Div1(t). Such means are formed, for example, by a conventional analog divider 26 as sold by Burr Brown under the reference DIV100KP.

It is also possible to use an analog-to-digital converter for performing the division function.

The effect of this first divider is to provide the following quotient:

$$\text{Div1}(t) = \frac{\text{Mes}(t)}{\text{Ref}(t)} = \frac{T \cdot (1 - p[\lambda(t)]) \cdot E(t)}{R \cdot E(t)}$$

i.e. Div1(t)=(T/R)−(T/R)p[λ(t)].

Figure 5:
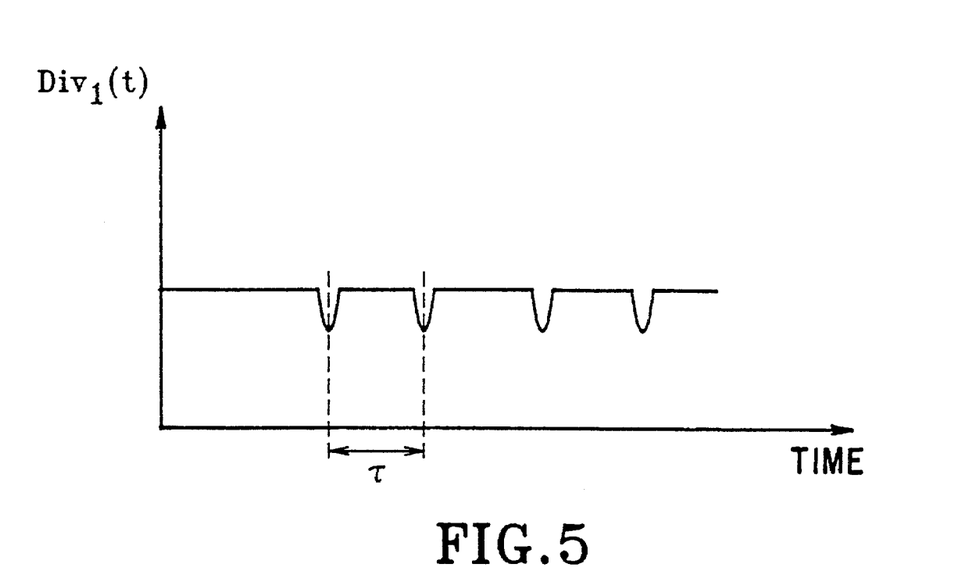
FIG. 5 shows the first quotient electrical signal.

The appearance of the first quotient electrical signal Div(t) is shown in FIG. 5 in which there can clearly be seen the inverted peaks representative of optical absorption by methane. This first quotient electrical signal comprises two portions: one of these portions is a time-varying portion referred as the "AC portion" and is equal to −(T/R)p[λ(t)], whereas the other portion does not vary with time, is referred to as the "DC portion" and is equal to (T/R). The apparatus of the invention provides for subsequent means to separate the AC and DC portions in the first quotient electrical signal Div1(t).

The above means may be constituted, for example, by a first electrical filter 28 which selects solely the AC portion of the signal Div1(t), and by a second electrical filter 30 which selects solely the DC portion of said signal Div1(t).

Figure 6A:
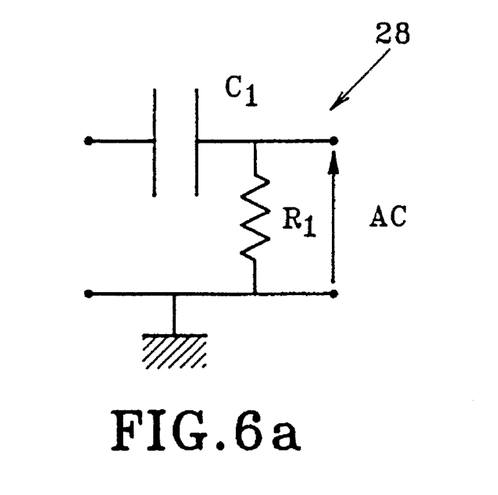
FIGS. 6a and 6b show respectively a highpass filter and a lowpass filter for selecting the time-varying AC portion and the non-time-varying DC portion of the first quotient electrical signal.
Figure 7:
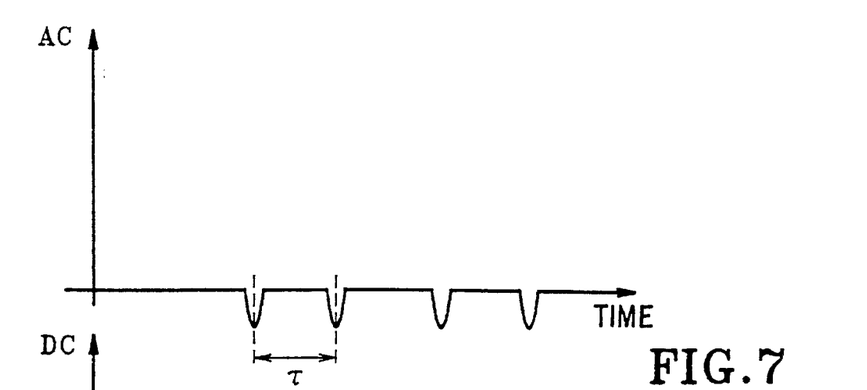
FIG. 7 shows the AC portion of the first quotient electrical signal.

As shown in FIG. 6a, the first electrical filter may be constituted, for example, by a series capacitor C1 having a capacitance of 0.1 μF associated with a parallel resistor R1 having a resistance of 1 kΩ, thereby forming a conventional highpass filter. The signal representative of the AC portion is shown in FIG. 7.

Figure 6B:
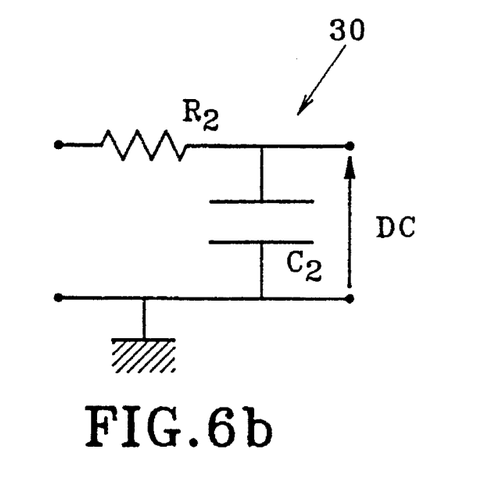
Figure 8:
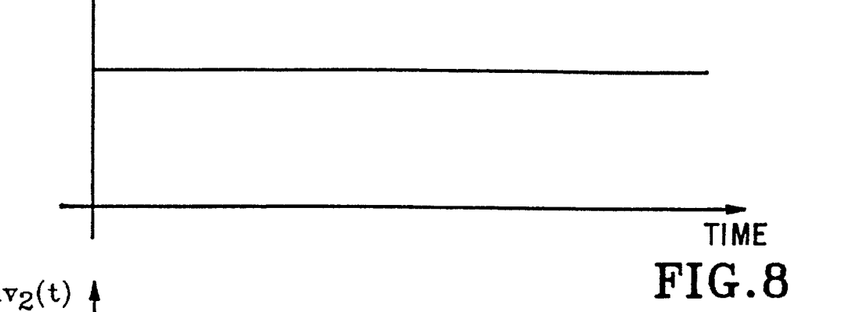
FIG. 8 shows the DC portion of the first quotient electrical signal.

The second electrical filter is constituted, for example, by a series resistor R2 having a resistance of 1 kΩ, and a parallel capacitor C2 having a capacitance equal to 0.1 μF, thereby forming an electrical lowpass filter (FIG. 6b). The signal representative of the DC portion is shown in FIG. 8.

Without going beyond the ambit of the present invention, it should be observed that it is also possible to use a first divider to divide the measurement signal by the reference signal a first time and then extract the AC portion from the quotient electrical signal while in parallel using a second divider to divide the measurement signal by the reference signal a second time, and then extract the DC portion from the resulting quotient electrical signal.

As shown in FIG. 1, the apparatus 1 of the invention includes a final element 32 constituted by a second divider for dividing the AC or time-varying portion of the quotient signal Div1(t) by the non-time-varying or DC portion of the same signal. This produces a second quotient electrical signal Div2(t). Such a divider can be constituted, for example, by a conventional analog divider circuit 32 sold by Burr Brown under the reference DIV100KP.

It would also be possible to use an analog-to-digital converter for performing this division function.

The effect of the second divider is to provide the following quotient:

$$\text{Div2}(t) = \frac{\text{AC}}{\text{DC}} = \frac{-(T/R)p[\lambda(t)]}{(T/R)}$$

i.e. Div2(t)=−p[λ(t)].

Figure 9:
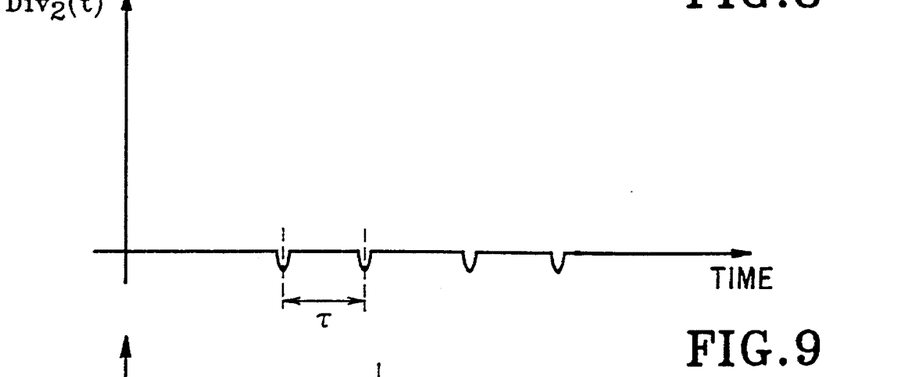
FIG. 9 shows the second quotient electrical signal.

The appearance of the second quotient electrical signal Div2(t) is given in FIG. 9. In this way, the resulting signal Div2(t) represents in absolute manner the contribution p[λ(t)] of the gas encountered on the overall optical path travelled by the optical radiation.

Advantageously, the values of optical absorption are absolute values for the wavelengths λ(t) and are therefore independent of the modulation from the laser diode and are thus insensitive to distortion in said laser diode. It is thus possible to stabilize the temperature of the laser diode and the electrical current flowing through its junction less accurately than in the prior art, and thus to use a power supply and wavelength modulation system 14 for the laser diode that is less sophisticated than those of the prior art.

It should also be observed that the signal processing performed after detecting the measurement and reference optical radiations could equally well be performed digitally.

In the above-described example relating to methane, once a signal has been obtained that represents solely the optical absorption of the gas, it then suffices to calculate the Rms value given below, e.g. by using a voltmeter, and to multiply the Rms value by a weighting coefficient available in known measurement tables so as to be able to deduce the concentration of methane in the cell 20.

$$\text{Rms value} = \sqrt{\int_{\lambda_0 - \Delta\lambda}^{\lambda_0 + \Delta\lambda} p^2[\lambda(t)] dt}$$

It should be observed that in order to implement a gas sensor, it is possible to calculate said Rms value at the output from the electrical filter 28 and subsequently to divide the signal −(T/R)Rms by the DC portion of the first quotient electrical signal in order to obtain the Rms value directly from the output of the divider 32.

Figure 10:
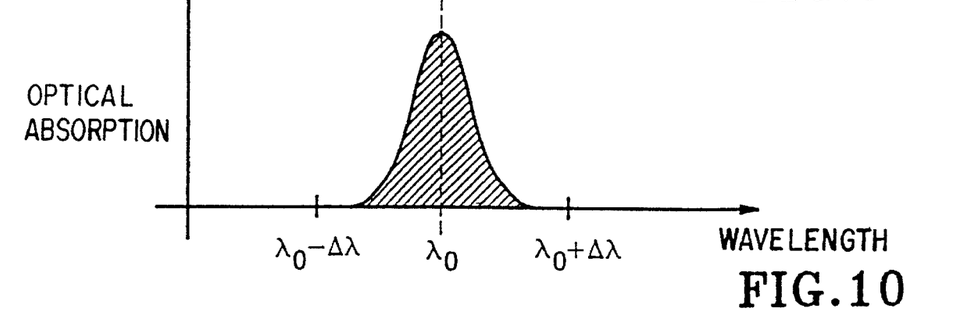
FIG. 10 shows a optical absorption line of methane.

As shown in FIG. 10, the Rms value corresponds, in fact, to the shaded area under the curve representative of optical absorption by methane over the predefined range of optical wavelengths, and is representative of an absorption peak at $\lambda^0 = 1.333$ μm. The invention thus makes it possible to calculate the concentration of a gas with the same resolution as in the prior art, but with greater accuracy.

Figure 11:
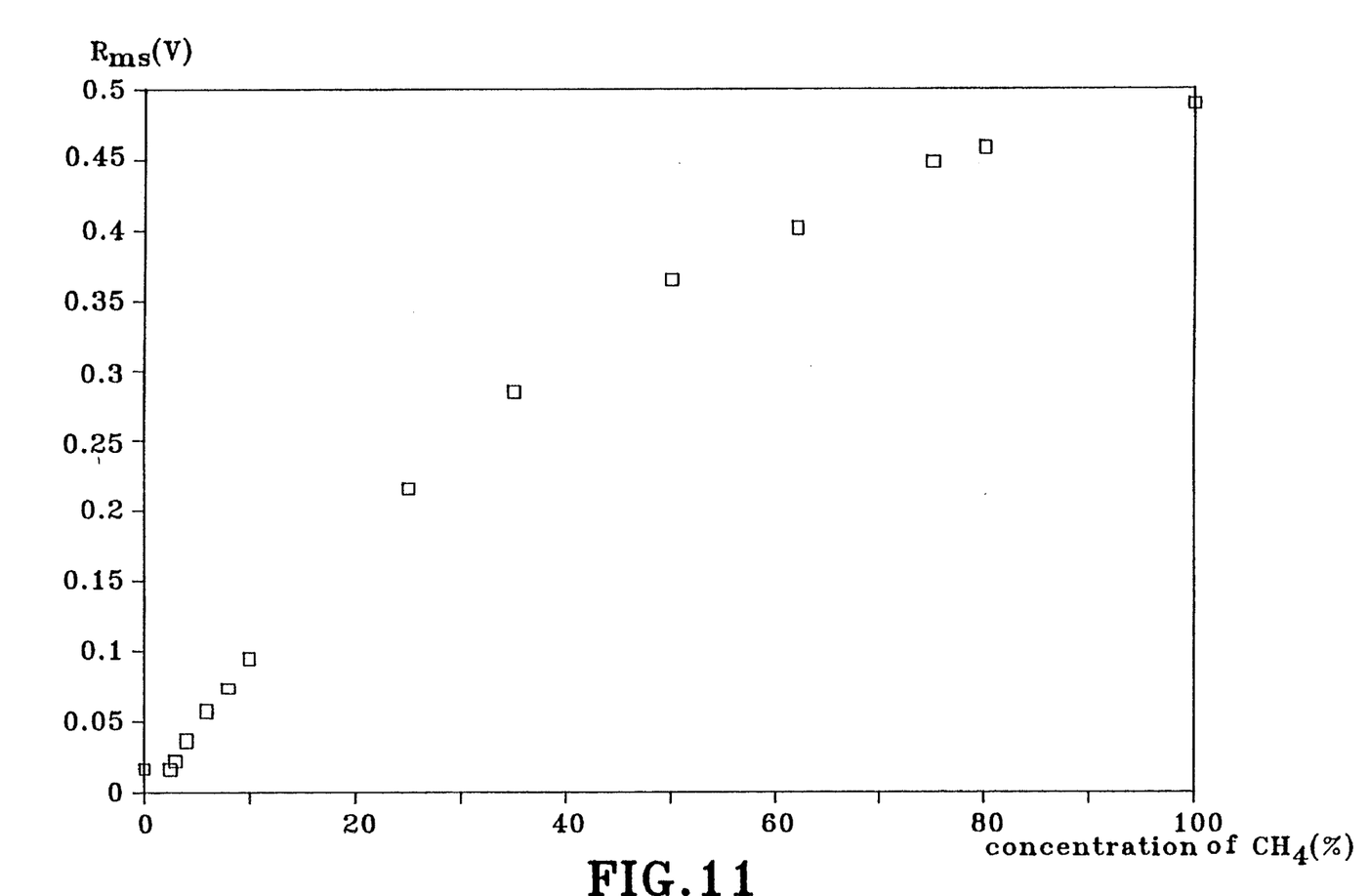
FIG. 11 shows the root-mean-square (Rms) value of the absorption signal for methane as a function of the concentration of said gas.

FIG. 11 plots Rms value of the output signal of the apparatus as a function of gas (methane) concentration, with the values obtained on this curve being attributable solely to the measured absorption. In contrast, when using the techniques of the prior art, it is possible to obtain the same curve as in FIG. 11, but there is no guarantee that the values obtained from the curve are metrologically adequate. In addition, the fact of having a metrological value for the concentration of a gas makes it possible, for example, to estimate quickly and reliably the heating power of the gas. It is also possible to detect a gas leak quickly, and for example to make provision for triggering a visual or an audible alarm if a leak is detected. The invention also makes it possible to ignore the influence of temperature and pressure on the gas.

Furthermore, the apparatus of the invention presents long term stability given that it continuously recalibrates itself without outside assistance, unlike the apparatus described in the prior art "Applied Optics" document in which it is necessary to perform manual balancing of the gains of both the measurement and the reference electrical signals. As a result, the apparatus of the invention can be used with advantage in various industries, and it can be installed in locations that are difficult of access, in which there is little room, and where there is no need to check its operation continuously. It may also be exposed to severe environments (pollution, vibration, . . . ) without endangering the metrological qualities of the measurements performed.

As shown in FIGS. 3, 5, 7, and 9, the time period t between two consecutive absorption peaks does not vary within a given signal, but may vary over time for various reasons associated with the operation of the laser diode. In conventional techniques, this variation constitutes a drawback since it spoils the quality of the measurement, and the apparatus mentioned in the "Applied Optics" document remedies the drawback by servo-controlling the emission wavelength of the laser on the absorption line of the gas.

Figure 12:
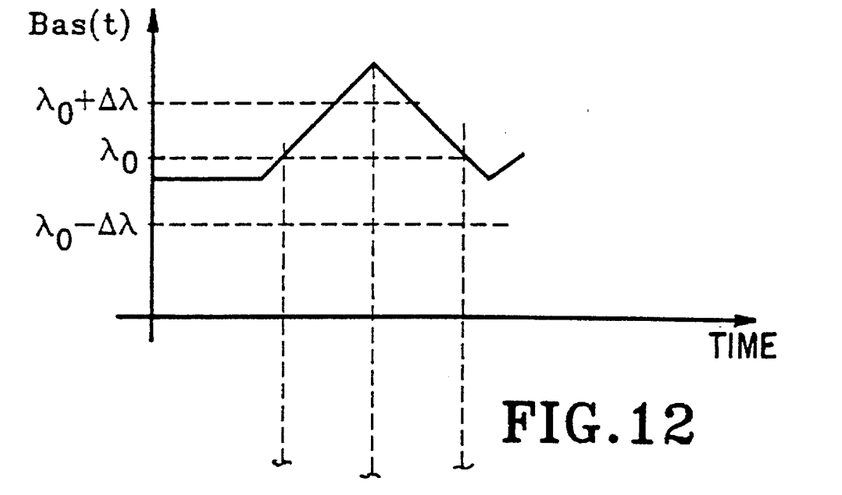
FIG. 12 shows how the signal of FIG. 2 changes over time.
Figure 13:
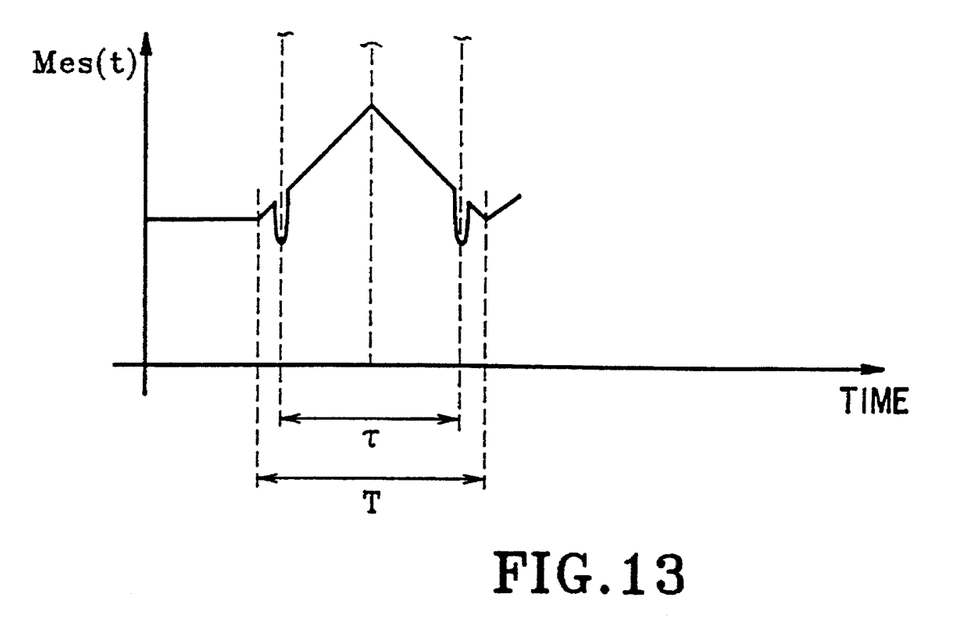
FIG. 13 shows how the signal of FIG. 3 changes over time.

Advantageously, using the apparatus of present invention, this time period may vary while the method is being applied, as shown in FIGS. 12 and 13 which show the resulting signals Bas(t) and Mes(t), without the metrological quality of the measurement being altered, and it is therefore unnecessary to provide additional equipment for servo-controlling the emission wavelength of the laser on the absorption line of the gas.

I claim:

1. A method of determining the absorption of electromagnetic radiation of wavelength that is variable over a range of wavelengths by a gas that presents selective absorption of said radiation in said range of wavelengths, the method consisting successively in:

producing two electromagnetic radiations of the same wavelength that is modulated as a function of time over the range of wavelengths, one of said electromagnetic radiations passing through said gas and being referred to as a "measurement" radiation, while the other electromagnetic radiation is referred to as a "reference" radiation;

detecting each of the measurement and reference electromagnetic radiations and transforming them into respective electrical signals referred to as a "measurement" signal Mes(t) and as a "reference" signal Ref(t);

dividing said measurement electrical signal Mes(t) by said reference electrical signal Ref(t), thereby obtaining a first quotient electrical signal Div1(t) made up of a time-varying AC portion and a non-time-varying DC portion;

separating said AC and DC portions; and dividing the AC portion of the first quotient electrical signal Div1(t) by the DC portion of the same signal in order to obtain a second quotient electrical signal Div2(t) representative solely of the absorption of electromagnetic radiation by said gas.

2. A method according to claim 1, wherein the two electromagnetic radiations are produced from a source that emits base electromagnetic radiation, which base electromagnetic radiation is split in order to obtain said measurement and reference electromagnetic radiations.

3. A method according to claim 1, wherein the electromagnetic radiation is optical radiation.

4. A method according to claim 2, wherein the electromagnetic radiation is optical radiation and wherein the source is a laser diode which is injection current and/or temperature modulated.

5. A method according to claim 1, wherein the AC and DC portions are separated by electrical filtering.

6. Apparatus for determining the absorption of electromagnetic radiation of wavelength variable over a range of wavelengths by a gas that presents selective absorption of said radiation in said range of wavelengths, and comprising:

means for producing two electromagnetic radiations of the same wavelength that is modulated as a function of time over the range of wavelengths, one of said electromagnetic radiations passing through said gas and being referred to as the "measurement" radiation, the other electromagnetic radiation being referred to as the "reference" radiation;

means for detecting each of the measurement and reference electromagnetic radiations and for transforming said radiations into respective electrical signals referred to as the "measurement" signal Mes(t) and as the "reference" signal Ref(t);

first divider for dividing the measurement electrical signal Mes(t) by the reference electrical signal Ref(t) so as to obtain a first quotient electrical signal Div1(t) constituted by a time-varying AC portion and a non-time-varying DC portion;

separator means for separating the AC and DC portions of the first quotient electrical signal; and second divider for dividing the AC portion of said first quotient electrical signal by the DC portion of the same signal in order to obtain a second quotient electrical signal Div2(t) representative solely of the absorption of the electromagnetic radiation by the gas.

7. Apparatus according to claim 6, wherein the means for producing two electromagnetic radiations comprise a source emitting base electromagnetic radiation Bas(t) together with splitting means for splitting said base radiation to obtain said measurement and reference electromagnetic radiations.

8. Apparatus according to claim 6, wherein the electromagnetic radiation is optical radiation.

9. Apparatus according to claim 7, wherein the electromagnetic radiation is optical radiation and wherein the splitting means are constituted by a glass plate placed on the path of the base optical radiation Bas(t) at an inclination to said radiation and possessing on that one of its faces which receives said signal a metal deposit in order to increase reflection from said face.

10. Apparatus according to claim 7, wherein the electromagnetic radiation is optical radiation and wherein the source is a laser diode provided with a system for modulating the optical wavelength of the base optical radiation by injection current and/or temperature modulation.

11. Apparatus according to claim 6, wherein the electromagnetic radiation is optical radiation and wherein the means for detecting the measurement and reference optical radiations and for transforming said radiations into electrical signals are constituted by photodiodes of the same type.

12. Apparatus according to claim 6, wherein the means for separating the AC and DC portions of the first quotient electrical signal Div1(t) comprise a first electrical filter for selecting the AC portion of said signal and a second electrical filter for selecting the DC portion of the signal.

13. Apparatus according to claim 12, wherein the first electrical filter is constituted by a capacitor and a resistor constituting a highpass filter.

14. Apparatus according to claim 12, wherein the second electrical filter is constituted by a resistor and a capacitor forming a lowpass filter.

* * * * *